(12) United States Patent
Natan (10) Patent No.: US 7,192,778 B2
(45) Date of Patent: Mar. 20, 2007

(54) SURFACE ENHANCED SPECTROSCOPY-ACTIVE COMPOSITE NANOPARTICLES

(76) Inventor: Michael J. Natan, 726 Casa Bonita Ct., Los Altos, CA (US) 94024

( * ) Notice: Subject to any disclaimer, the term of this patent is extended or adjusted under 35 U.S.C. 154(b) by 623 days.

(21) Appl. No.: 10/345,821

(22) Filed: Jan. 16, 2003

(65) Prior Publication Data

US 2003/0166297 A1     Sep. 4, 2003

Related U.S. Application Data (63) Continuation-in-part of application No. 09/680,782, filed on Oct. 6, 2000, now Pat. No. 6,514,767.

(60) Provisional application No. 60/157,931, filed on Oct. 6, 1999, provisional application No. 60/190,395, filed on Mar. 17, 2000.

(51) Int. Cl.
*G01N 37/00* (2006.01)

(52) U.S. Cl. .............................. 436/56; 436/73; 436/80; 436/166; 436/525; 436/527

(58) Field of Classification Search ...................... None
See application file for complete search history.

(56) References Cited

U.S. PATENT DOCUMENTS

| | | | |
|---|---|---|---|
| 5,023,139 A | 6/1991 | Birnboim et al. | |
| 5,266,498 A | 11/1993 | Tarcha et al. | |
| 5,445,972 A | 8/1995 | Tarcha | |
| 5,609,907 A | 3/1997 | Natan | |
| 5,825,790 A | 10/1998 | Lawandy | |
| 5,828,450 A | 10/1998 | Dou et al. | |
| 6,149,868 A | 11/2000 | Natan et al. | |
| 6,219,137 B1 | 4/2001 | Vo-Dinh | |
| 6,603,537 B1 | 8/2003 | Dietz et al. | |
| 6,687,395 B1 | 2/2004 | Dietz et al. | |
| 6,699,724 B1 | 3/2004 | West et al. | |
| 6,750,016 B2 | 6/2004 | Mirkin et al. | |

FOREIGN PATENT DOCUMENTS

| | | |
|---|---|---|
| WO | WO 98/04740 | 2/1998 |
| WO | WO 98/10289 | 3/1998 |
| WO | WO 99/21934 | 5/1999 |
| WO | WO 01/08081 | 2/2000 |
| WO | WO 00/11024 | 3/2000 |
| WO | WO 02/079764 | 10/2002 |

OTHER PUBLICATIONS

Akbarian et al. (1996) J. Raman Spectroscopy 27:775-783.
Chan et al. (1998) Science 281:2016-2018.
Emory et al. (1997) Analytical Chemistry 69:2631-2635.
Emory et al. (1998) J. Phys Chem. B 102:493-497.
Emory et al. (1998) J. American Chemical Society 120:8009-8010.

(Continued)

*Primary Examiner*—Yelena G. Gakh
(74) *Attorney, Agent, or Firm*—Swanson & Bratschun, L.L.C.

(57) ABSTRACT

Metal nanoparticles associated with a spectroscopy-active (e.g., Raman-active) analyte and surrounded by an encapsulant are useful as sensitive optical tags detectable by surface-enhanced spectroscopy (e.g., surface-enhanced Raman spectroscopy).

32 Claims, 4 Drawing Sheets

OTHER PUBLICATIONS

Grabar et al. (1995) Analytical Chemistry 67:735-743.
Kneipp et al. (1998) Exp. Techn. Phys. 36 2:161-166.
Kneipp et al. (1995) Applied Spectroscopy 49:780-784.
Kneipp et al. (1996) Phys. Rev. Letters 76:2444-2447.
Kneipp et al. (1997) Phys. Rev. Letters 78:1667-1670.
Kneipp et al. (1998) Applied Spectroscopy 52:175-178.
Kneipp et al. (1998) Applied Spectroscopy 52:1493-1497.
Kneipp et al. (1998) Phys. Rev. B 57:6281-6284.
Kneipp et al. (1999) Chem. Review 99:2957-2975.
Kneipp et al. (1999) Current Science 77:915-924.
Lyon et al. (1997) Anal. Chem. 69:3400-3405.
Nie et al. (1997) Science 275:1102-1106.
Nie et al. (1997) Annu. Rev. Biophys. Biomol. Struct. 26:567-596.
Stober et al. (1968) J. Colloid Interface Sci. 26:62-69.
Ung et al. (1998) Langmuir 14:3740-3748.
Shibata et al. (1998) J. Sol-Gel technol 11:279-287.
Felidj et al. (1998) New J. Chem 725-732.
Freeman et al. (1996) J. Phys Chem. 100:718-724.
Van Duyne et al. (1993) J. Chem. Phys. 99:2101-2115.
Ni et al. (1999) Anal. Chem. 71(21):4903.
Liz-Marzan et al. (1996) Langmuir 12:4329.
Ung et al. (1998) Langmuir 14:3740.
Bruchez et al. (1998) Science 281:2013.
Chan and Nie (1998) Science 281:2016.
Vo-Dinh (1998) 17(8-9):XP002314222.

SURFACE ENHANCED SPECTROSCOPY-ACTIVE COMPOSITE NANOPARTICLES

CROSS-REFERENCE TO RELATED APPLICATIONS

This application is a continuation-in-part of U.S. patent application Ser. No. 09/680,782, filed Oct. 6, 2000, entitled "Surface Enhanced Spectroscopy-Active Composite Nanoparticles," now U.S. Pat. No. 6,514,767 and incorporated herein by reference, which claims priority to U.S. Provisional Application No. 60/157,931, filed Oct. 6, 1999, entitled "Glass Coated Surface Enhanced Raman Scattering Tags," and U.S. Provisional Application No. 60/190,395, filed Mar. 17, 2000, entitled "GANS Particles."

FIELD OF THE INVENTION

This invention relates generally to submicron-sized tags or labels that can be covalently or non-covalently affixed to entities of interest for the purpose of quantification, location, identification, or tracking. More particularly, it relates to surface enhanced spectroscopy-active composite nanoparticles, methods of manufacture of the particles, and uses of the particles.

BACKGROUND OF THE INVENTION

When light is directed onto a molecule, the vast majority of the incident photons are elastically scattered without a change in frequency. This is termed Rayleigh scattering. However, the energy of some of the incident photons (approximately 1 in every $10^7$ incident photons) is coupled into distinct vibrational modes of the molecule's bonds. Such coupling causes some of the incident light to be inelastically scattered by the molecule with a range of frequencies that differ from the range of the incident light. This is termed the Raman effect. By plotting the frequency of such inelastically scattered light against its intensity, the unique Raman spectrum of the molecule under observation is obtained. Analysis of the Raman spectrum of an unknown sample can yield information about the sample's molecular composition.

The incident illumination for Raman spectroscopy, usually provided by a laser, can be concentrated to a small spot if the spectroscope is built with the configuration of a microscope. Since the Raman signal scales linearly with laser power, light intensity at the sample can be very high in order to optimize sensitivity of the instrument. Moreover, because the Raman response of a molecule occurs essentially instantaneously (without any long-lived highly energetic intermediate states), photobleaching of the Raman-active molecule—even by this high intensity light—is impossible. This places Raman spectroscopy in stark contrast to fluorescence spectroscopy, in which photobleaching dramatically limits many applications.

The Raman effect can be significantly enhanced by bringing the Raman-active molecule(s) close ($\leq 50$ Å) to a structured metal surface; this field decays exponentially away from the surface. Bringing molecules in close proximity to metal surfaces is typically achieved through adsorption of the Raman-active molecule onto suitably roughened gold, silver or copper or other free electron metals. Surface enhancement of the Raman activity is observed with metal colloidal particles, metal films on dielectric substrates, and with metal particle arrays. The mechanism by which this surface-enhanced Raman scattering (SERS) occurs is not well understood, but is thought to result from a combination of (i) surface plasmon resonances in the metal that enhance the local intensity of the light, and; (ii) formation and subsequent transitions of charge-transfer complexes between the metal surface and the Raman-active molecule.

SERS allows detection of molecules attached to the surface of a single gold or silver nanoparticle. A Raman enhancing metal nanoparticle that has associated or bound to it a Raman-active molecule(s) can have utility as an optical tag. For example, the tag can be used in immunoassays when conjugated to an antibody against a target molecule of interest. If the target of interest is immobilized on a solid support, then the interaction between a single target molecule and a single nanoparticle-bound antibody can be detected by searching for the Raman-active molecule's unique Raman spectrum. Furthermore, because a single Raman spectrum (from 100 to 3500 $cm^{-1}$) can detect many different Raman-active molecules, SERS-active nanoparticles may be used in multiplexed assay formats.

SERS-active nanoparticles with adsorbed Raman-active molecules offer the potential for unprecedented sensitivity, stability, and multiplexing functionality when used as optical tags in chemical assays. However, metal nanoparticles present formidable practical problems when used in such assays. They are exceedingly sensitive to aggregation in aqueous solution; once aggregated, it is not possible to re-disperse them. In addition, the chemical compositions of some Raman-active molecules are incompatible with the chemistries used to attach other molecules (such as proteins) to metal nanoparticles. This restricts the choices of Raman-active molecules, attachment chemistries, and other molecules to be attached to the metal nanoparticle.

SUMMARY OF THE INVENTION

One embodiment of the present invention provides surface-enhanced spectroscopy (SES)-active composite nanoparticles, such as SERS-active composite nanoparticles (SACNs). Such nanoparticles each contain a SES-active metal nanoparticle; a submonolayer, monolayer, or multilayer of spectroscopy-active species associated with or in close proximity (e.g., adsorbed) to the metal surface; and an encapsulating shell made of a polymer, glass, or any other dielectric material. This places the spectroscopy-active molecule (alternately referred to herein as the "analyte," not to be confused with the species in solution that is ultimately being quantified) at the interface between the metal nanoparticle and the encapsulant.

In some embodiments, the encapsulant is glass. The resulting glass-coated analyte-loaded nanoparticles (GANs) retain the activity of the spectroscopy-active analyte, but lightly sequester this activity from the exterior surface of the nanoparticle. Thus, in the case of surface-enhanced Raman scattering (SERS), the resulting GAN exhibits SERS activity, but the Raman-active analyte is located at the interface between the metal nanoparticle and the encapsulant.

The analyte molecule can be chosen to exhibit extremely simple Raman spectra, because there is no need for the species to absorb visible light. This, in turn, allows multiple composite nanoparticles, each with different analyte molecules, to be fabricated such that the Raman spectrum of each analyte can be distinguished in a mixture of different types of particles.

Surface-enhanced spectroscopy (SES)-active composite nanoparticles are easily handled and stored. They are also aggregation resistant, stabilized against decomposition of the analyte in solvent and air, chemically inert, and can be centrifuged and redispersed without loss of SERS activity. SACNs may be provided as a dispersion in suitable solvent for storage or association with an object or molecule.

In one embodiment, the encapsulant may be readily derivatized by standard techniques. This allows the particles to be conjugated to molecules (including biomolecules such as proteins and nucleic acids) or to solid supports without interfering with the Raman activity of the particles. Unlike metal nanoparticles, SACNs can be evaporated to dryness and then completely redispersed in solvent. Using the techniques provided herein, it is possible to fabricate particles that are individually detectable using SERS.

In an alternative embodiment, SACNs are attached to, mixed with, or otherwise associated with objects for tracking, identification, or authentication purposes. Each type of particle or group of particle types, as defined by the Raman spectrum of the encapsulated analyte, represents a particular piece of information. Tagged objects are verified by acquiring their Raman spectrum. Any liquid, solid, or granular material can be tagged with a SACN. By associating an object with more than one different SACN type, a large number of distinct SACN groups can be obtained.

BRIEF DESCRIPTION OF THE FIGURES

FIG. 5 shows Raman spectra of GANs (80 nm Au core/2-mercaptopyridine/20 nm glass) and of a 50 mM solution of 2-mercaptopyridine absorbed onto a conventional three-layer SERS substrate.

DETAILED DESCRIPTION OF EMBODIMENTS

Various embodiments of the present invention are directed to surface-enhanced spectroscopy-active composite nanoparticles (SACNs), including surface-enhanced Raman spectroscopy (SERS)-active composite nanoparticles. Other embodiments provide methods of manufacture of the particles and methods of use of the particles. These submicron-sized tags or labels can be covalently or non-covalently affixed to or mixed with entities of interest, ranging in size from molecular to macroscopic, for the purpose of quantification, location, identification, or tracking.

The SACNs provided by embodiments of the present invention are uniquely identifiable nanoparticles. They can be used in virtually any situation in which it is necessary to label molecules or objects with an optical tag. Biomolecules can be conjugated readily to the exterior of SACNs by standard techniques, thereby allowing the particles to function as optical tags in biological assays. SACNs can be used in virtually any assay that uses an optical tag, such as a fluorescent label. However, as optical tags, SACNs have several distinct advantages over fluorescent labels. These advantages include vastly more sensitive detection, chemical uniformity, and the absolute resistance of the SERS activity to photobleaching or photodegradation. A further benefit of using SACNs as optical tags is the ease with which individual SACNs having different SERS activities may be resolved from one another. At least twenty different SACNs are resolvable from one another using a simple Raman spectroscope. This enables multiplexed assays to be performed using a panel of different SACNs, each having a unique and distinguishable SERS activity. It also provides for, when SACNs are formed into groups, a very large number of unique SACN combinations with which objects can be labeled.

A surface-enhanced spectroscopy-active composite nanoparticle (SACN) contains a surface-enhanced spectroscopy (SES)-active (e.g., SERS-active) metal nanoparticle that has attached to or associated with its surface one or more spectroscopy-active (e.g., Raman-active) molecules (alternately referred to herein as "analytes"). This complex of Raman-enhancing metal and analyte is then coated or encapsulated by an encapsulant. A SACN typically has a diameter of less than 200 nm or, alternatively, less than 100 nm. Each SACN is identified by the distinct Raman spectrum of its Raman-active analyte. Note that a metal nanoparticle is referred to as "surface-enhanced spectroscopy active" because it acts to enhance the spectroscopic signal of the associated analyte; it is the signal of the analyte, which is inherently spectroscopy active, that is being measured.

SACNs can be produced by growing or otherwise placing a shell of a suitable encapsulant over a SERS-active metal nanoparticle core with associated Raman-active analyte. The metal nanoparticle core can be, for example, a gold or silver sphere of between about 20 nm and about 200 nm in diameter. In another embodiment, the metal nanoparticle has a diameter of between about 40 nm and about 100 nm. In an alternative embodiment, the metal nanoparticle is an oblate or prolate metal spheroid. For SERS using red incident light (~633 nm), a suitable SERS response can be obtained with 63 nm diameter gold nanoparticles, but other particle diameters can also be employed. Typically, a SACN contains only one metal nanoparticle, but more than one particle can be encapsulated together if desired. In a collection or plurality of SACNs, some may have one metal nanoparticle and some more than one metal nanoparticle. In this collection of particles, at least some of the detected Raman signal originates from the particle or particles containing only one metal nanoparticle. Because the Raman signal intensity is a substantially linear function of the number of Raman-active analytes, limiting a group of SACNs to a known number of metal nanoparticles and adsorbed analyte molecules allows estimation of the number of particles from the signal intensity of a group of particles.

The metal nanoparticles can contain any SES-active metal, i.e., any metallic substance for which chemical enhancement, electromagnetic enhancement, or both, is known in the art. For example, the metal nanoparticles can contain Au, Ag, or Cu. Other suitable metals include, but are not limited to, Na, K, Cr, Al, or Li. The metal particles can also contain alloys of metals. In one embodiment, the metal nanoparticle consists of a core (of pure metal or an alloy) overlaid with at least one metal shell. In this case, the composition of the outer layer can be chosen to maximize the intensity of the Raman signal from the analyte.

Metal nanoparticles of the desired size can be grown as metal colloids by a number of techniques well known in the art. For example, chemical or photochemical reduction of metal ions in solution using any number of reducing agents has been described. Likewise, nanoparticle syntheses have been carried out in constrained volumes, e.g. inside a vesicle. Nanoparticles can also be made via electrical discharge in solution. Dozens of other methods have been described, dating back to the mid-1800's.

The Raman-active analyte can be any molecular species having a measurable SERS spectrum. Whether or not a spectrum is measurable may depend upon the instrument with which the spectrum is acquired and the amount of adsorbed analyte. In general, however, a measurable spectrum is one that is detectable in the presence of the metal nanoparticle and encapsulant and can be recognized as characteristic of the particular analyte. Typically, the maximum intensity of the SERS spectrum of the analyte is substantially greater than that of the particle without the analyte (i.e., the metal nanoparticle and encapsulant). Aromatic molecules often have measurable Raman spectra. Examples of aromatic molecules suitable for use as analytes in embodiments of SACNs include, but are not limited to, trans-1,2-bis(4-pyridyl)ethylene (BPE), pyridine, 2-mercaptopyridine, furonitrile, imidazole, and para-nitroso-N,N'-dimethylaniline (p-NDMA).

Those skilled in the art will recognize that there is a great deal of latitude in the composition of an analyte that yields a distinct Raman spectrum. For example, in some embodiments, the analyte is not a molecule: it can be a positively or negatively charged ion (e.g., $Na^+$ or $CN^-$). If the analyte is a molecule, it can be neutral, positively charged, negatively charged, or amphoteric. The analyte can be a solid, liquid or gas. Non-molecular species such as metals, oxides, sulfides, etc. can serve as the Raman-active species. Any species or collection of species that gives rise to a unique Raman spectrum, whether solid, liquid, gas, or a combination thereof, can serve as the analyte. Examples easily number in the many millions and include but are not limited to Hg, dimethylformamide, HCl, $H_2O$, $CN^-$, polypyrrole, hemoglobin, oligonucleotides, charcoal, carbon, sulfur, rust, polyacrylamide, citric acid, and diamond. In the case of diamond, the unique phonon mode of the particle can be used. For hemoglobin, only the porphyrin prosthetic group exhibits significant Raman activity; thus, complex substances can be used as the analyte if only part of the molecular or atomic complexity is present in the Raman spectrum.

The analyte can also be a polymer to which multiple Raman-active moieties are attached. In this case, differentiable SACNs contain the same polymer serving as the analyte, but the polymers have different attached moieties yielding different Raman spectra. The polymer backbone does not itself contribute to the acquired Raman spectrum. In one embodiment, the polymer is a linear chain containing amine groups to which Raman-active entities are attached.

Alternatively, the polymer can be a dendrimer, a branched polymer with a tightly controlled tree-like structure, with each branch terminating in a Raman-active species. A suitable dendrimer structure has four generations of branches terminating in approximately 45 Raman-active entities.

Note that SACNs that give rise to unique Raman spectra can be considered different even if the analyte is essentially the same. For example, the Raman spectrum of a cationic polymer charge compensated by anions can change depending on the choice of counter ion. A panel of differentiable SACNs can be formed using this polymer as a component of the analyte; each unique SACN has the polymer charge-compensated by a different anion, thereby endowing each SACN with a unique Raman spectrum. In addition, a given analyte may have different Raman shifts on different SERS-active layers, and differentiable SACNs can be formed using the same analyte sandwiched between layers of different metals. For example, p-NDMA has different Raman shifts on gold and silver surfaces. Alternatively, one or more bands in the Raman spectrum of an analyte may be dependent on the density of the analyte in the SACN. SACNs formed with different densities of the same analyte are therefore differentiable from one another.

As will be apparent to one skilled in the art, characteristics of some suitable Raman-active analytes are (i) strong Raman activity, which minimizes the number of molecules needed to provide a given signal strength; and (ii) simple Raman spectrum, which allows a large number of unique SACNs to be distinguished when used simultaneously.

The Raman-active analyte can form a sub-monolayer, a complete monolayer, or a multilayer assembly on the surface of the metal nanoparticle core. A Raman-active analyte can be a single species of Raman-active molecule, a mixture of different species of Raman-active molecules, or a mixture of Raman-active molecules and molecules without measurable Raman activity.

Typically, the encapsulant does not measurably alter the SERS activity of the metal nanoparticle or the Raman spectrum of the analyte. In an alternative embodiment, however, the encapsulant can have a measurable effect without adding significant complexity to the Raman spectrum. The encapsulant can be readily modified in order to attach molecules, including biomolecules, to its exterior surface. Suitable encapsulants include, but are not limited to, glass, polymers, metals, metal oxides (such as $TiO_2$ and $SnO_2$), and metal sulfides. The encapsulation is carried out after, or during, adsorption to the core nanoparticle of the Raman-active analyte that is to provide the Raman activity of the SACN. In this way, the Raman-active analyte is sequestered from the surrounding solvent. Such a configuration provides the metal nanoparticle core with stable SERS activity. Alternatively, it may not be necessary to sequester the analyte completely, in which case the encapsulant does not completely surround the metal nanoparticle and analyte.

The thickness of the encapsulant can be easily varied depending on the physical properties required of the SACN. For example, coatings that are too thick—on the order of 1 micron or more—might preclude obtaining intense Raman spectra. Coatings too thin might lead to interference in the Raman spectrum of the analyte by molecules on the encapsulant surface. Raman scattering intensity decreases exponentially with distance between analyte and nanoparticle surface; beyond 2 nm, the enhancing effect is negligible. An encapsulant that is at least this thick prevents interference in the spectrum from molecules on the outside of the SACN. Physical properties such as sedimentation coefficient will clearly be affected by the thickness of encapsulant. In general, the thicker the encapsulant, the more effective the sequestration of the Raman-active analyte(s) on the metal nanoparticle core from the surrounding solvent. One suitable thickness range of the encapsulant is between about 1 nm and about 40 nm. Alternatively, the encapsulant can be between about 5 nm and about 15 nm thick. Another suitable thickness range is between about 10 nm and about 20 nm.

In one embodiment of the invention, the encapsulant is glass (e.g., $SiO_x$). To encapsulate in glass, the metal nanoparticle cores are preferably treated first with a glass primer (that is, a material that can lead to growth of a uniform coating of glass, or can improve adhesion of the glass coat to the particle, or both). Glass is then grown over the metal nanoparticle by standard techniques well known in the art. The resulting SACNs are referred to as glass analyte-loaded nanoparticles (GANs). For GANs, a suitable glass thickness ranges from about 1 nm to about 40 nm or, alternatively, between about 10 nm and about 20 nm. In one embodiment, the GAN contains a 60 nm diameter gold particle encapsulated by a 16 nm thick shell of glass. In an alternative embodiment, the encapsulant is $TiO_2$, which is chemically similar to $SiO_2$ and commonly used in many industries.

It may be desirable to separate true SACNs from free particles of encapsulant that were not nucleated around a metal nanoparticle. Such separation improves the SERS activity of the nanoparticle preparation because free encapsulant particles are not SERS active. For example, GANs can be separated from free glass particles by size-exclusion centrifugation in 50% glycerol.

Note that glass and many other materials contain functional groups amenable to molecular attachment. For example, immersion of glass in base allows covalent attachment of alkyl trichlorosilanes or alkyl trialkoxysilanes, with additional functionality available on the end of the alkyl group. Thus, glass surfaces can be modified with all forms of biomolecules and biomolecular superstructures including cells, as well as oxides, metals, polymers, etc. Likewise, surfaces of glass can be modified with well-organized monomolecular layers. In short, glass coatings support essentially any and all forms of chemical functionalization (derivatization). This is equally true for many different forms of encapsulant, so that SACNs can be affixed to any species with chemically reactive functionality. All chemical functional groups are reactive under certain conditions. There is thus no limitation to the species that can be immobilized on the encapsulant surface.

The optimization of the dimensions of the SACNs is readily accomplished by one skilled in the art. Accordingly, one might alter the composition of the particle, or its size and shape, in accordance with the invention to optimize the intensity of the Raman signal. Indeed, it is known that core-shell nanoparticles (i.e. Au/AuS) support SERS and have very different optical properties compared to pure metal nanoparticles. Likewise, it is known that SERS from prolate spheroids is enhanced relative to spheres with the same major axis. It is further known that single particle enhancements are strongly wavelength-dependent. Thus, one might "tune" the particle size, shape, and composition to achieve maximum signal for a given excitation wavelength.

One embodiment of the present invention contemplates the formation of a panel of at least 20 different SACNs, each having a unique SERS spectrum. This panel is referred to herein as a collection of distinguishable particles. Because the Raman bands of many molecules are extremely narrow (for example, $CN^-$ is less than 1 nm at FWHM), it is possible to synthesize a panel of SACNs, each containing a Raman analyte that is spaced 20 wavenumbers away in the spectrum from its closest neighbor. For example, a GAN with $^{13}CN$ as the analyte is easily distinguished from a GAN with $^{12}CN$ as the analyte, and as well easily distinguishable from one with $C^{15}N$. In this way, it is possible to form 540 distinct and easily resolvable peaks in a single Raman spectrum at 633 nm from 300 to 3000 $cm^{-1}$ using a spectrograph to spread the photons and a CCD camera as a detector. In general, Raman-active analytes can be used that have isotopic compositions distinct from naturally abundant species. For example, as described above, $^{13}CN$ is completely resolvable from any natural $^{12}CN$ that may be present in the background. Of course, those skilled in the art will recognize that combinations of isotopes as well as ratios of isotopes can be equally effectively used to identify unique SACNs.

Raman experiments with GANs or other SACNs can also be carried out with visible or near-IR irradiation, make use of Raman bands from 100 $cm^{-1}$ to 5000 $cm^{-1}$, employ any form of monochromator or spectrometer to spatially or temporally resolve photons, or employ any form of photon detector. This arrangement facilitates the synthesis of panels of at least 10 resolvable SACNs, and provides ample bandwidth for literally hundreds of panels of SACNs.

Although the SERS activity of each population of SACNs in the panel is unique, the other properties of the SACNs are kept uniform across the panel. Because the SERS activity of each SACN is sequestered from the surrounding milieu by the encapsulant, individual populations do not have different solvent or storage requirements. Also, each SACN has the same exterior shell, simplifying the choice of chemistry either for attachment of molecules to the SACNs or attachment of the SACNs to solid supports.

While the examples above have focused on Raman scattering, and in particular surface-enhanced Raman scattering as the detection mechanism, a number of analogous methods can apply equally well and are included within the scope of the present invention. For example, one can employ a resonantly-excited analyte, thus making the technique surface-enhanced resonance Raman scattering (SERRS). One could also take advantage of existing methods of surface-enhanced infrared absorption spectra (SEIRA) from nanoscale roughened surfaces. Likewise, surface-enhanced hyper-Raman scattering (SEHRS) also occurs at nanoscale roughened metal surfaces, and this technique as well as its resonant analogue SEHRRS can be employed. Note that for a given molecule, with either $3N-5$ or $3N-6$ unique vibrations, where N is the number of atoms, all vibrations can be found in either the Raman, hyperRaman, or infrared spectrum. Indeed, identification of certain SACNs could rest on a combination of optical interrogation methods, including SERS, SERRS, SEIRA, SEHRS and SEHRRS.

Note also that a significant amount of (Rayleigh) light scattering is known to occur from particles with dimensions at least $1/10$ the exciting wavelength, thus creating the possibility that Rayleigh or hyperRayleigh scattering could be used in identification of SACNs. Moreover, combinations of elastic scattering (e.g. Rayleigh), inelastic scattering (e.g. Raman), and absorption (e.g. IR) could be used to identify particles.

Use of SACNs

The SACNs provided by embodiments of the present invention can be used in virtually any application in which a detectable tag or label is required. In some embodiments, SACNs are used in biological and chemical assays as replacements for standard fluorescent tags. Indeed, SACNs possess a number of characteristics that make them far superior to prior art optical tags based on fluorophores. For example, assays using fluorophore detection are commonly hampered by the presence of autofluorescence and other background effects. In addition, many assays require use of a number of different fluorophores; different fluorophores commonly require different attachment chemistries and have different environmental requirements and sensitivities. Particularly noteworthy is the quenching of fluorescent activity that is observed when some fluorophores are conjugated to proteins. Finally, irreversible photodegradation resulting from the creation of a triplet or singlet excited state, followed by a non-reversible chemical reaction that permanently eliminates the excited state, places a severe limitation on the sensitivity of detection. By contrast, SACNs cannot be photobleached or photodegraded, they have uniform chemical and physical properties, and they can be readily resolved from the background. Perhaps most importantly, SACN detection is significantly more sensitive than fluorophore detection. Indeed, it is possible to tag a single molecule with a single SACN, and then detect the presence of that molecule using Raman spectroscopy. Such simple single molecule resolution is without parallel in the fluorophore detection art.

An example of a biological assay in which SACNs can be used as optical tags is the sandwich immunoassay. In sandwich assays, a target to be detected is captured by a solid surface. An antibody (or other ligand) to the same target is attached to a SACN, and then contacted with the solid support. The presence of the SACN SERS signal at the solid support indicates the presence of the antigen. In general, SACNs can be conjugated to any molecule that is used to detect the presence of a specific target in an assay.

In a specifically contemplated embodiment, SACNs are conjugated to nucleic acid molecules. In this way, they can be used in virtually any assay known in the art that detects specific nucleic acid sequences using optically-tagged nucleic acid probes.

SACNs are especially suitable for multiplexed chemical assays in which the identity of SACNs encodes the identity of the target of the assay. Prior art multiplexed assays that use fluorophores to encode target identity are subject to a number of severe constraints imposed by the physical and chemical properties of the fluorophores. Specifically, different fluorophores have different excitation maxima, so coincident excitation of multiple fluorescent tags is not possible. Moreover, fluorescence emission occurs in broad spectral bands, so the bands from one fluorophore often overlap with those of another. As a result, resolving even three different fluorescence activities requires sophisticated optics to separate and then detect the individual emission wavelengths. Because of these problems, multiplexed assays that use fluorophores rely on positional information to reveal target identity. Often, multiplexed assays with fluorophores use a solid support on which ligands are arranged in defined positions. The location of fluorophore signal reveals the identity of the target; the size of the fluorophore signal at that location indicates the amount of the target. However, the synthesis of solid supports with reagents localized at specific positions is expensive and time-consuming. Also, there are limits on the number of features that may be defined on a single surface.

By contrast, the SACNs of the present invention offer remarkable spectral diversity and resolvability. As a result, SACNs can be used in multiplexed assays to yield quantitative and qualitative information without requiring the position-specific localization of reagents. Each SACN coupled to a target-specific reagent can encode the identity of that specific target, and the intensity of a particular Raman signal reveals the quantity of that target. For example, in the sandwich immunoassays described above, the identity of targets captured on the solid support can be determined by using a different flavor of SACN for each target.

Although SACNs are perfectly suited for use in multiplexing applications, they need not be used to encode identity in this manner. They can be used simply as replacements for fluorophores in multiplexed assays in which reagents are localized to specific positions on solid supports. When used in this way, the SACNs offer vastly more sensitive target detection than fluorophores.

In other embodiments, SACNs serve as tags for labeling objects or materials, e.g., for anti-counterfeiting or authentication purposes, or for encoding the history of an object moving through a manufacturing process or supply chain. In these applications, one or more SACNs are associated with an object or material and later "read" by Raman spectroscopy to determine the identity of the particle or particles and obtain information about the tagged object. The acquired spectrum can be compared to a reference spectrum or to a spectrum of the particles acquired before they were associated with the object. If necessary, suitable corrections can be made to account for background emission from the object. Authentication can occur at any desired point during the lifetime of the object, e.g., upon receipt of a manufactured object by a retailer or upon sale of an antique object.

Each SACN or group of SACNs, with its unique Raman spectrum, corresponds to or represents a particular piece of information. Any type of information can be represented by a SACN, depending upon the application. For example, a SACN or group of SACNs can represent an individual object such as an item of sports memorabilia, a work of art, an automobile, or the item's owner or manufacturer; a class of objects, such as a particular formulation of pharmaceutical product; or a step of a manufacturing process. The information represented by a particular Raman spectrum or SACN type can be stored in a database, computer file, paper record, or other desired format.

The small, robust, non-toxic, and easily-attachable nature of SACNs allows their use for tagging virtually any desired object. The tracked object can be made of solid, liquid, or gas phase material or any combination of phases. The material can be a discrete solid object, such as a container, pill, or piece of jewelry, or a continuous or granular material, such as paint, ink, fuel, or extended piece of, e.g., textile, paper, or plastic, in which case the particles are typically distributed throughout the material.

Examples of specific materials or objects that can be tagged with SACNs include, but are not limited to:

Packaging, including adhesives, paper, plastics, labels, and seals

Agrochemicals, seeds, and crops

Artwork

Computer chips

Cosmetics and perfumes

Compact disks (CDs), digital video disks (DVDs), and videotapes

Documents, money, and other paper products (e.g., labels, passports, stock certificates)

Inks, paints, and dyes

Electronic devices

Explosives

Food and beverages, tobacco

Textiles, clothing, footwear, designer products, and apparel labels

Polymers

Hazardous waste

Movie props and memorabilia, sports memorabilia and apparel
Manufacturing parts
Petroleum, fuel, lubricants, oil
Pharmaceuticals and vaccines Particles can be associated with the material in any way that maintains their association at least until the particles are read. Depending upon the material to be tagged, the particles can be incorporated during production or associated with a finished product. Because they are so small, the particles are unlikely to have a detrimental effect on either the manufacturing process or the finished product. The particles can be associated with or attached to the material via any chemical or physical means. For example, particles can be mixed with and distributed throughout a liquid-based substance such as paint, oil, or ink and then applied to a surface. They can be wound within fibers of a textile, paper, or other fibrous or woven product, or trapped between layers of a multi-layer label. The particles can be incorporated during production of a polymeric or slurried material and bound during polymerization or drying of the material. Additionally, the surfaces of the particles can be chemically derivatized with functional groups of any desired characteristic, as described above, for covalent or non-covalent attachment to the material. When the particles are applied to a finished product, they can be applied manually by, e.g., a pipette, or automatically by a pipette, spray nozzle, or the like. Particles can be applied in solution in a suitable solvent (e.g., ethanol), which then evaporates.

SACNs have a number of inherent properties that are advantageous for tagging and tracking applications. They offer a very large number of possible codes. For example, if a panel of SACNs is constructed with 20 distinguishable Raman spectra, and an object is labeled with two SACNs, there are 20*19/2=190 different codes. If the number of particles per object is increased to 5, there are 15,504 possible codes. Ten particles per object yields $1.1 \times 10^6$ different codes. A more sophisticated monochromator increases the number of distinguishable Raman spectra to, e.g., 50, greatly increasing the number of possible codes.

SACNs can be identified using a conventional Raman spectrometer. In fact, one benefit of using SACNs is the versatility of excitation sources and detection instrumentation that can be employed for Raman spectroscopy. Visible or near-IR lasers of varying sizes and configurations can be used to generate Raman spectra. Portable, handheld, and briefcase-sized instruments are commonplace. At the same time, more sophisticated monochromators with greater spectral resolving power allow an increase in the number of unique taggants that can be employed within a given spectral region. For example, the capability to distinguish between two Raman peaks whose maxima differ by only 3 $cm^{-1}$ is routine.

Typically, if a suitable waveguide (e.g., optical fiber) is provided for transmitting light to and from the object, the excitation source and detector can be physically remote from the object being verified. This allows SACNs to be used in locations in which it is difficult to place conventional light sources or detectors. The nature of Raman scattering and laser-based monochromatic excitation is such that it is not necessary to place the excitation source in close proximity to the Raman-active species.

Another characteristic of SACNs is that the measurement of their Raman spectra need to strictly be confined to "line of sight" detection, as with, e.g., fluorescent tags. Thus their spectrum can be acquired without removing the particles from the tagged object, provided that the material is partially transparent to both the excitation wavelength and the Raman photon. For example, water has negligible Raman activity and does not absorb visible radiation, allowing SACNs in water to be detected. SACNs can also be detected when embedded in, e.g., clear plastic, paper, or certain inks.

SACNs also allow for quantitative verification, because the Raman signal intensity is an approximately linear function of the number of analyte molecules. For standardized particles (uniform analyte distribution), the measured signal intensity reflects the number or density of particles. If the particles are added at a known concentration, the measured signal intensity can be used to detect undesired dilution of liquid or granular materials.

SACNs are chemically and biologically inert, and a glass coating gives the particles charge, flow, and other physical properties similar to those of $SiO_2$ particles commonly used as excipients in pills, vitamins, and a wide variety of other materials. A $TiO_2$ coating on SACNs allow them to be used in the very large number of materials that currently contain $TiO_2$, such as papers, paints, textiles, and apparel.

Because of their submicron size, SACNs can be added to fluids without changing the fluid properties significantly or affecting the fluid handling equipment. For example, the particles can flow through narrow tubes and be expelled out nozzles without clogging lines or orifices.

SACNs are also non-toxic and can be ingested safely by humans and other animals. This enables their tagging of pharmaceutical products, food products, and beverages (e.g., wine). Particles are comparable in size to the excipients normally used as vehicles for drugs.

The following examples are offered by way of illustration and not by way of limitation.

WORKING EXAMPLES

Working Example 1

Synthesis of Glass-Coated Analyte-Loaded Nanoparticles (GANs)

Materials: Water used for all preparations was 18.2 MΩ, distilled through a Barnstead nanopure system. Snake skin dialysis tubing, 3,500 MWCO, was purchased from Pierce. 3-aminopropyltrimethoxysilane (APTMS), 3-mercaptotrimethoxysilane (MPTMS), and 3-mercaptopropylmethyldimethoxysilane (MPMDMS) were obtained from United Chemical. $HAuCl_4.3H_2O$, trisodium citrate dihydrate, sodium hydroxide, trans-1,2-bis(4-pyridyl)ethylene (BPE), pyridine, 2-mercaptopyridine, sodium silicate, tetraethyl orthosilicate (TEOS), and ammonia were obtained from Sigma-Aldrich. BPE was recrystallized several times before use. Dowex cation exchange resin (16–40 mesh) was obtained from J. T. Baker. Pure ethyl alcohol (EtOH) was purchased from Pharmco.

Colloid preparation: 12-nm colloidal Au (nearly spherical, with a standard deviation less than 2 nm) was prepared from $HAuCl_4.3H_2O$ reduced by citrate as described in Grabar et al, Analytical Chemistry 67:735–743 (1995), incorporated herein by reference in its entirety.

Colloid >12 nm was prepared as follows: 3 ml of 12 mM $HAuCl_4$ was added for every 97 ml of $H_2O$. The solution was then brought to a boil under vigorous stirring and 1 ml of 12-nm Au colloid as a seed and 0.5 ml of 1% sodium citrate per 100 ml of $HAuCl_4$ solution was added and boiled for 10 minutes. The size of the resulting particles was determined by transmission electron microscopy using Gatan or NIH Image software. Finally, the citrate ions surrounding the Au colloid were removed with dialysis, 7 exchanges of at least 4 hours each.

GANs preparation: All reactions were performed in plastic Erlenmeyer flasks. Any amount of colloid could be used in a preparation and the subsequent reactants added in appropriate amounts based on the surface area and concentration of the Au colloid.

A typical experiment used 25 ml of dialyzed, 50-nm, 0.17 nM Au colloid. The pH of the colloid was adjusted from 5 to 7 with the addition of 50 µL of 0.1 M NaOH. The colloid was rendered vitreophilic with the addition 125 µL of 0.5 mM MPTMS (or APTMS, or MPMDMS). After 15 minutes of magnetic stirring, 167 µL of a 0.5 mM solution of the Raman tag (BPE, pyridine, or 2-mercaptopyridine) was added. During another 15 minute period of stirring, a 0.54% solution of active silica was prepared by mixing 1 g of sodium silicate with 50 ml of 3 M NaOH and lowering the pH to 10 with cation exchange resin. One ml of the active silica was added and the resulting solution was approximately pH 9. The solution remained stirring for 15 minutes and then was allowed to stand.

After a 24 hour period, 100 ml of EtOH was added to the solution to proceed with silica growth via the method described in Stöber et al, J. Colloid Interface Sci. 26: 62 (1968), incorporated herein by reference in its entirety. Growth of ~4 nm of additional glass shell was accomplished with the addition of 15 µL of TEOS and 125 µL of ammonia. The reaction was stirred for 15 minutes and then allowed to stand for at least 12 hours. The addition of TEOS and ammonia was continued until the desired shell thickness was obtained.

Working Example 2

Transmission Electron Microscopy of GANs

Figure 1A:
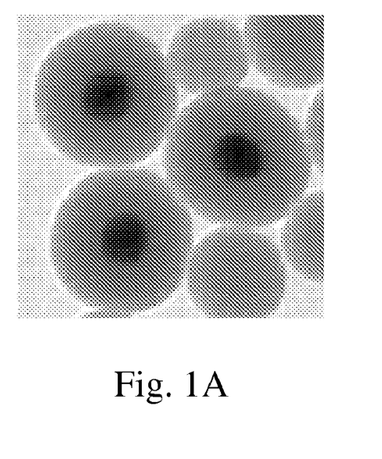
FIG. 1A is a transmission electron micrograph of GANs with 35 nm Au cores and 40 nm glass shells.
Figure 1B:
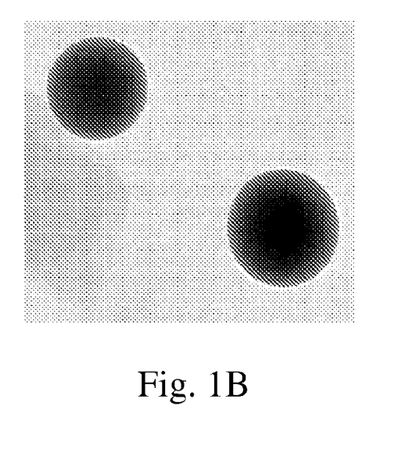
FIG. 1B is a transmission electron micrograph of GANs with 35 nm Au cores and 16 nm glass shells.
Figure 2:
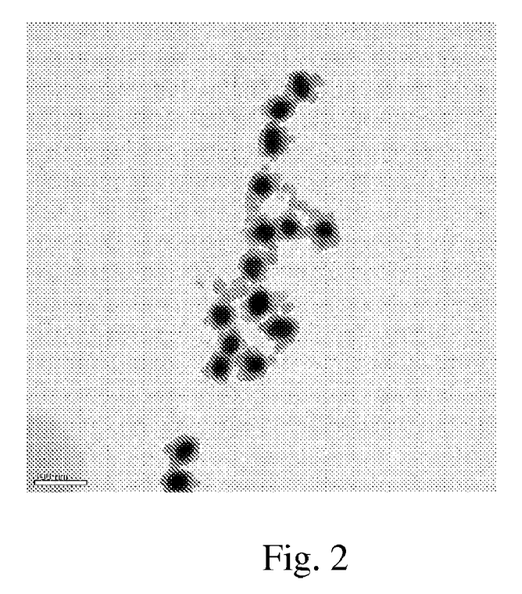
FIG. 2 is a transmission electron micrograph of 35 nm Au, 8 nm glass GANs following centrifugation in a 50% glycerol solution.

Transmission electron microscopy (TEM) images were taken of preparations of GANs; these TEM images illustrate the uniformity of GANs preparations. FIG. 1A shows GANs containing 35 nm Au cores with 40 nm glass. FIG. 1B shows 60 nm Au cores with 16 nm glass. FIG. 2 illustrates 35 nm Au, 8 nm glass GANs following centrifugation through a 50% glycerol solution.

Working Example 3

Demonstration of the Sequestration of the Metal Core from Solvent

Figure 3A:
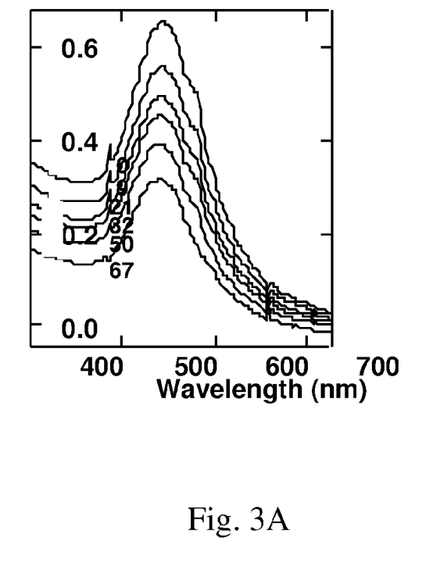
FIGS. 3A and 3B are plots of absorbance versus wavelength, for different etch times, and absorbance versus etch time at a single wavelength, respectively, for a particle having a 35 nm Au core and 8 nm glass shell.
Figure 3B:
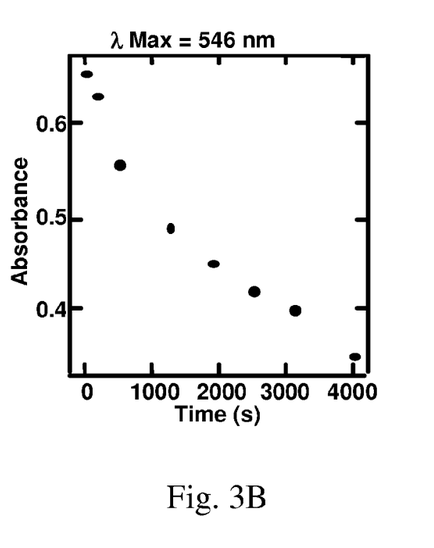

For GANs to function in diverse chemical environments, it is necessary that the Raman-active analyte be sequestered from the surrounding solvent. To demonstrate this sequestration, one may look at diffusion rates through the glass network. This is done by monitoring the rate at which aqua regia (3 HCl:1 HNO$_3$) is able to etch out the Au core of a GAN. FIG. 3 demonstrates one such experiment for a batch of GANs particles with a 35 nm Au core, and 8 nm shell of glass. To 500 µl of ≈0.17 nM GANs was added 200 µl of an etch solution (50 µl HNO$_3$ and 150 µl HCl). The absorbance of the solution was measured ($\lambda_{max}$ 546 nm) at various times after addition of the etch solution. Etching of the gold core results in a decrease in the absorbance; this is plotted in FIG. 3A (the time after the addition of the etch solution is indicated). The rate of Au etching is shown in FIG. 3B as a plot of absorbance versus time in etch solution (right). Additional studies performed by the inventors have shown that etching of a Au core by aqua regia does not occur with a 20 nm glass shell over a four hour time period.

Working Example 4

SERS Spectra of GANs Particles

Figure 4:
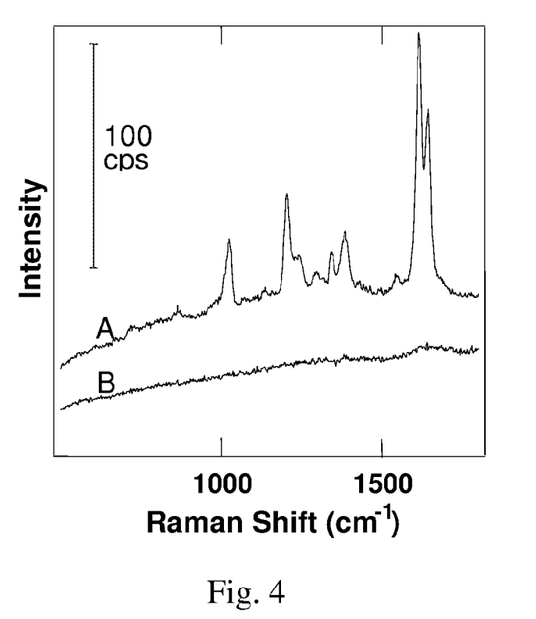
FIG. 4 shows Raman spectra of GANs with a 40 nm Au core encapsulated in 4 mm of glass, with (trace A) and without (trace B) the Raman-active analyte, trans-1,2-bis(4-pyridyl)ethylene (BPE).

GANs containing a 40 nm Au core coated with trans-1, 2-bis(4-pyridyl)ethylene (BPE) encapsulated in 4 nm of glass were synthesized and examined by Raman spectroscopy. The Raman spectrum obtained using 20 mW of 632.8 nm excitation, with a 3 mm lens and 30 second integration is plotted in FIG. 4. Trace A on the graph shows the characteristic BPE Raman signal; trace B shows the Raman signal from the same particles without the BPE analyte. It can be seen that the GANs without the BPE analyte give essentially no Raman signal.

Working Example 6

Figure 5:
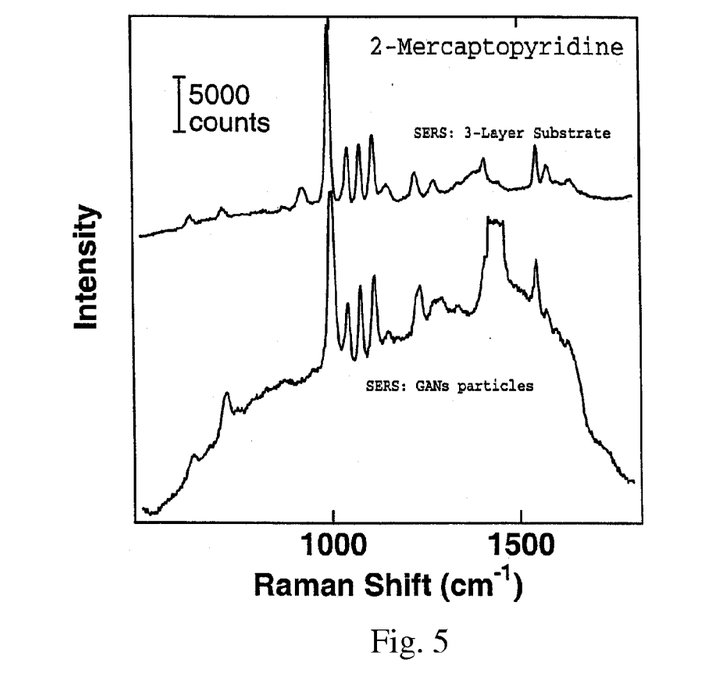
FIG. 5 shows SERS of the supernatant fluid after the (A) first, (B) second, and (C) third centrifugation step. Trace (A) is SERS spectrum of ethanol, which is the solvent used to prepare the particles. Traces (B) and (C) are the spectra after resuspension in $H_2O$. Conditions: 20 mW of 632.8 nm excitation, 3-mm lens, 30-s of integration.

Comparison of SERS Spectra of Raman-Active Analytes on GANs with other SERS Substrates GANs (80 nm Au core/20 nm glass) containing 2-mercaptopyridine as the Raman-active analyte were analyzed by Raman spectroscopy using 25 mW of 632.8 nm excitation with a 3 mm lens and 60 seconds of integration. The Raman spectrum of the GANs preparation was then compared with the Raman spectrum obtained when a 50 mM solution of 2-mercaptopyridine is absorbed onto a conventional three-layer SERS substrate (25 mW 632.8 nm excitation, 3 mm lens, 30-seconds integration). FIG. 5 shows the two Raman spectra. It can be seen that the two spectra have identical features and intensities, illustrating that the metal nanoparticles of the GANs are effective SERS substrates.

Working Example 7

SERS Spectra of GANs with Mixtures of Raman-Active Analytes

Figure 6:
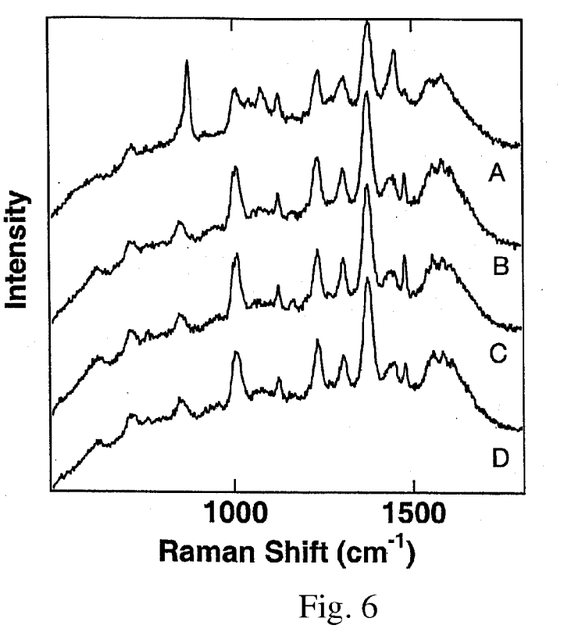
FIG. 6 shows Raman spectra of the following four types ("flavors") of GANs particles: (A) GANs tagged with furonitrile; (B) GANs tagged with furonitrile (66%) and cyanoacetic acid (33%); (C) GANs tagged with furonitrile (33%) and cyanoacetic acid (66%); and (D) GANs tagged with cyanoacetic acid.

SERS spectra of the following four flavors of GANs particles were obtained using 26 mW of 632.8 nm excitation, a 3-mm lens, and 30-second integration: (A) GANs tagged with furonitrile; (B) GANs tagged with furonitrile (66%) and cyanoacetic acid (33%); (B) GANs tagged with furonitrile (33%) and cyanoacetic acid (66%); and (D) GANs tagged with cyanoacetic acid. The percentages indicated are the relative concentrations of each compound in the tagging solution added. FIG. 6 shows that the furonitrile and cyanoacteic acid have relatively the same signal intensity and have similar spectral profiles. The fact that the spectra of B and C are very similar to the spectrum of D indicates that cyanoacetic acid has a better affinity for the Au nanoparticle than furonitrile.

Working Example 9

Tagging Paper with GANs

GANs were prepared from 12 nm-diameter gold particles coated with trans-1,2bis-(4-pyridyl)ethylene (BPE) or para-nitroso-N,N'-dimethylaniline (p-NDMA) as described in Working Example 1. Encapsulation was completed with a single addition of TEOS and ammonia. Particles were stored in ethanol as prepared (at a concentration of approximately 1 nM).

The particle solutions were mixed and three spots each of approximately 10–20 μl of the resulting solution were pipetted onto yellow and white sheets of conventional paper. After evaporation of ethanol, spots were visible on both sides of the paper, indicating that the particles had penetrated the sheets.

Figure 7A:
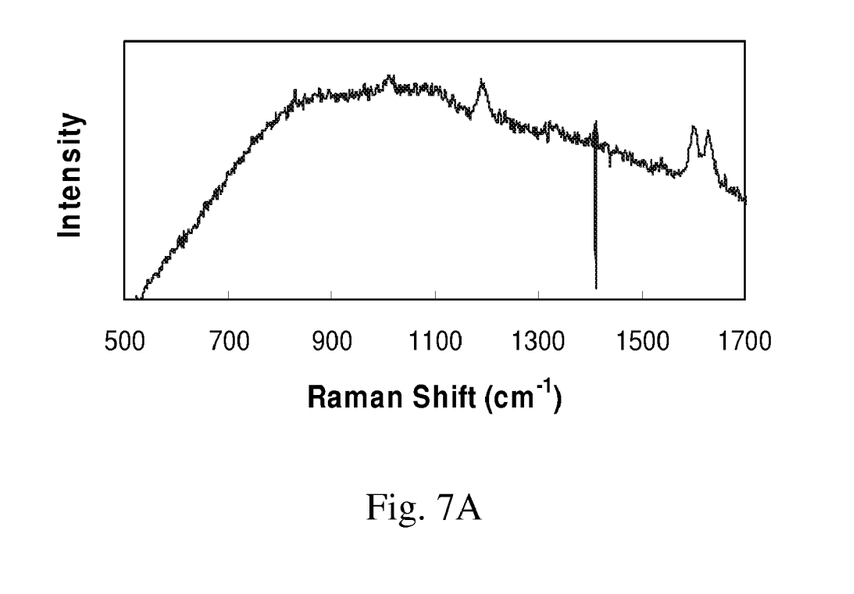
FIGS. 7A and 7B show Raman spectra of GANs containing BPE and para-nitroso-N,N'-dimethylaniline (p-NDMA) in ethanol spotted onto white and yellow paper, respectively.
Figure 7B:
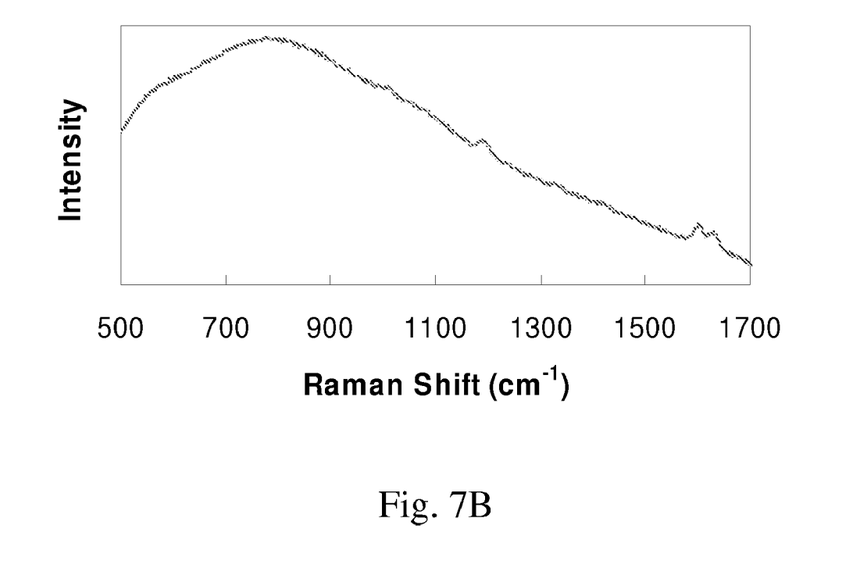

Raman spectra of the spots were acquired using approximately 20 mW of 633 nm excitation with a 3 mm lens and 30 seconds of integration. FIG. 7A shows a representative spectrum on white paper and FIG. 7B on yellow paper. Both the yellow and white paper displayed high levels of background fluorescence. However, characteristic peaks of BPE at about 1200, 1610, and 1640 $cm^{-1}$ were detectable over the background signal in both cases.

It should be noted that the foregoing description is only illustrative of the invention. Various alternatives and modifications can be devised by those skilled in the art without departing from the invention. Accordingly, the present invention is intended to embrace all such alternatives, modifications and variances which fall within the scope of the disclosed invention.

What is claimed is:

1. A particle comprising: a surface-enhanced spectroscopy (SES) active metal nanoparticle, a SES active label associated with said SES-active metal nanoparticle, and an encapsulant for reducing aggregation surrounding said SES-active metal nanoparticle and said SES-active label, wherein said encapsulant comprises a material selected from the group consisting of glass, polymers, metal oxides, and metal sulfides, and wherein said particle has a measurable SES spectrum.

2. The particle of claim 1, wherein said metal nanoparticle comprises a metal selected from the group consisting of Au, Ag, Cu, Na, Al, and Cr.

3. The particle of claim 2, wherein said metal nanoparticle comprises Au.

4. The particle of claim 2, wherein said metal nanoparticle comprises Ag.

5. The particle of claim 1 wherein said metal nanoparticle comprises an alloy of metals selected from the group consisting of Au, Ag, Cu, Na, Al, and Cr.

6. The particle of claim 1, wherein said metal nanoparticle has a diameter less than about 200 nm.

7. The particle of claim 6, wherein said metal nanoparticle has a diameter between about 20 nm and about 200 nm.

8. The particle of claim 7, wherein said metal nanoparticle has a diameter between about 40 nm and about 100 nm.

9. The particle of claim 1, wherein said metal nanoparticle is a sphere.

10. The particle of claim 1, wherein said metal nanoparticle is an oblate spheroid.

11. The particle of claim 1, wherein said metal nanoparticle is a prolate spheroid.

12. The particle of claim 1, wherein said encapsulant has a thickness less than about 1 micron.

13. The particle of claim 12, wherein said encapsulant has a thickness between about 1 nm and about 40 nm.

14. The particle of claim 13, wherein said encapsulant has a thickness between about 5 nm and about 15 nm.

15. The particle of claim 1, wherein said encapsulant comprises a plurality of materials.

16. The particle of claim 1, wherein said encapsulant comprises glass ($SiO_x$).

17. The particle of claim 1, wherein said encapsulant comprises $TiO_2$.

18. The particle of claim 1, wherein said spectroscopy-active label forms a partial monolayer coating on said metal nanoparticle.

19. The particle of claim 1, wherein said spectroscopy-active label forms a monolayer coating on said metal nanoparticle.

20. The particle of claim 1, wherein said spectroscopy-active label forms a multilayer coating on said metal nanoparticle.

21. The particle of claim 1, wherein said measurable SES spectrum is a spectrum obtained by a method selected from the group consisting of surface-enhanced Raman spectroscopy, surface-enhanced resonance Raman spectroscopy, surface-enhanced hyperRaman spectroscopy, surface-enhanced resonance hyperRaman spectroscopy, and surface-enhanced infared spectroscopy.

22. The particle of claim 1, wherein said spectroscopy-active analyte is an aromatic analyte.

23. A particle comprising a gold nanoparticle having a diameter of between about 20 nm and about 100 nm, a surface-enhanced spectroscopy (SES)-active label associated with said gold nanoparticle, and glass having a thickness of between about 1 nm and about 15 nm surrounding said gold nanoparticle and said SES-active label, wherein said SES-active label has a measurable SES spectrum.

24. The particle of claim 23 wherein said measurable SES spectrum is a spectrum obtained by a method selected from the group consisting of surface-enhanced Raman spectroscopy, surface-enhanced resonance Raman spectroscopy, surface-enhanced hyperRaman spectroscopy, surface-enhanced resonance hyperRaman spectroscopy, and surface-enhanced infared spectroscopy.

25. A particle comprising a surface-enhanced spectroscopy (SES) active metal nanoparticle, an aromatic label adsorbed on the surface of said (SES) active metal nanoparticle, and an encapsulant for reducing aggregation surrounding said (SES) active metal nanoparticle and said aromatic label, wherein said encapsulant comprises a material selected from the group consisting of glass, polymers, metal oxides, and metal sulfides.

26. The particle of claim 25, wherein said metal nanoparticle comprises a metal selected from the group consisting of Au, Ag, Cu, Na, Al, and Cr.

27. The particle of claim 25, wherein said metal nanoparticle has a diameter less than about 200 nm.

28. The particle of claim 27, wherein said metal nanoparticle has a diameter of between about 20 nm and about 200 nm.

29. The particle of claim 28, wherein said metal nanoparticle has a diameter of between about 40 nm and about 100 nm.

30. The particle of claim 25 wherein said encapsulant has a thickness less than about 1 micron.

31. The particle of claim 30 wherein said encapsulant has a thickness of about 1 nm and about 40 nm.

32. The particle of claim 31 wherein said encapsulant has a thickness of between about 5 nm and about 15 nm.

* * * * *